(12) United States Patent
Rae et al.

(10) Patent No.: US 11,253,794 B2
(45) Date of Patent: Feb. 22, 2022

(54) UNIVERSAL BLOOD PRODUCT AND METHODS OF PREPARING AND USING SAME

(71) Applicant: IMMUTRIX THERAPEUTICS, INC., Rapid City, SD (US)

(72) Inventors: Carol A. Rae, Rapid City, SD (US); Jan S. Simoni, Rapid City, SD (US); John F. Moeller, Rapid City, SD (US)

(73) Assignee: Proprietary Technology Assets, LLC, Rapid City, SD (US)

( * ) Notice: Subject to any disclaimer, the term of this patent is extended or adjusted under 35 U.S.C. 154(b) by 0 days.

(21) Appl. No.: 15/545,233

(22) PCT Filed: May 27, 2016

(86) PCT No.: PCT/US2016/034679
§ 371 (c)(1),
(2) Date: Jul. 20, 2017

(87) PCT Pub. No.: WO2016/191691
PCT Pub. Date: Dec. 1, 2016

(65) Prior Publication Data
US 2018/0065062 A1 Mar. 8, 2018

Related U.S. Application Data

(60) Provisional application No. 62/167,743, filed on May 28, 2015.

(51) Int. Cl.
*B01D 15/20* (2006.01)
*B01D 15/38* (2006.01)
(Continued)

(52) U.S. Cl.
CPC .............. *B01D 15/20* (2013.01); *A61K 35/14* (2013.01); *B01D 15/34* (2013.01);
(Continued)

(58) Field of Classification Search
CPC .......... B01D 15/34; B01D 15/20; B01J 20/20; B01J 20/048; A61K 35/14; A61K 35/00; A61P 7/00
See application file for complete search history.

(56) References Cited

U.S. PATENT DOCUMENTS

2006/0105472 A1* 5/2006 Teng ................ G01N 33/54393
436/518
2008/0132688 A1 6/2008 Zhou
(Continued)

FOREIGN PATENT DOCUMENTS

CN 1634138 A 7/2005
CN 107709547 A 2/2018
(Continued)

OTHER PUBLICATIONS

Filing Receipt and Specification for provisional application entitled "Universal Blood Plasma and Methods of Preparing and Using Same," by Carol A. Rae, et al., filed May 28, 2015 as U.S. Appl. No. 62/167,743.
(Continued)

*Primary Examiner* — Tracy Vivlemore
*Assistant Examiner* — Nam P Nguyen
(74) *Attorney, Agent, or Firm* — Barnes & Thornburg LLP

(57) ABSTRACT

A method of preparing a universal blood product comprising obtaining a blood product; contacting the blood product with (i) hydroxyapatite; (ii) a carbonaceous material comprising at least a mixture of a first carbon particle having macroporous size α and a second carbon particle having macroporous size β; and (iii) at least one support matrix chemically associated with an antigenic determinant. to form a cleansed product; and recovering the cleansed product. A method of preparing a universal blood product comprising obtaining a blood product; contacting the blood product with (i)
(Continued)

hydroxyapatite; (ii) a carbonaceous material comprising at least a mixture of a first carbon particle having macroporous size $\alpha$ and a second carbon particle having macroporous size $\beta$; and (iii) at

UNIVERSAL BLOOD PRODUCT AND METHODS OF PREPARING AND USING SAME

CROSS-REFERENCE TO RELATED APPLICATIONS

This application is a filing under 35 U.S.C. 371 of International Application No. PCT/US2016/034679 filed May 27, 2016, entitled "Universal Blood Product and Methods of Preparing and Using Same," which claims priority to U.S. Provisional Patent Application No. 62/167,743 filed May 28, 2015, which applications are incorporated by reference herein in their entirety.

TECHNICAL FIELD

Generally disclosed herein are compositions, systems, and methods for the removal of molecules from a biological fluid that may elicit an undesirable physiological response that may when said fluid is administered to a subject. More specifically disclosed herein are compositions, systems, and methods for the preparation of a universal blood product.

BACKGROUND

Human plasma is a source of over 700 proteins, many of them with considerable therapeutic value such as albumin, clotting factors (Factor VIII, IX, XIII, prothrombin, fibrinogen, von Willebrandt factor), immunoglobulins (Ig), protease inhibitors, and others. Therapeutic plasma is obtained from whole blood donated by volunteers using well-established blood bank separation techniques. These techniques although effective in removal of viral and bacterial pathogens are ineffective in removal of autoantibodies and disease mediators such as inflammatory cytokines, and the like. There are many examples that plasma from one donor who is a carrier of undiagnosed and asymptomatic autoimmune disease can contaminate a large pool of plasma and expose many recipients to these disease mediators. A similar situation could exist with undiagnosed and asymptomatic blood donors who carry high levels of inflammatory cytokines and other active molecules formed in metabolic diseases.

Examination of a number of standard pools of plasma showed that a proportion contained 'immune' anti-A or anti-B antibodies. Anti-A antibodies are originated from the immune response towards influenza virus, whose epitopes are similar enough to be antigenic. Anti-B antibodies are reactive against antigen found on red blood cells, and may also be formed against bacterial antigens. The anti-A and anti-B antibodies are usually immunoglobulins with a molecular weights ranging from about 100 kDa to about 1000 kDa and pIs ranging from 5.5-7.4. These antibodies may under certain conditions produce undesirable clinical and hematological side-effects. The presence in plasma of Anti-A and Anti-B antibodies significantly limits the overall plasma donor pool and necessitates time consuming screening tests, complicating blood transfusions.

There exists an ongoing need for compositions and methods able to effectively produce a universal blood product.

SUMMARY

Disclosed herein is a method of preparing a universal blood product comprising obtaining a blood product wherein the blood product comprises whole blood or plasma; contacting the blood product with (i) hydroxyapatite; (ii) a carbonaceous material comprising at least a mixture of a first carbon particle having macroporous size $\alpha$ and a second carbon particle having macroporous size $\beta$; and (iii) at least one support matrix chemically associated with an antigenic determinant. to form a cleansed product; and recovering the cleansed product.

Also disclosed herein is a method of preparing a universal blood product comprising obtaining a blood product wherein the blood product comprises whole blood or plasma; contacting the blood product with (i) hydroxyapatite; (ii) a carbonaceous material comprising at least a mixture of a first carbon particle having macroporous size at and a second carbon particle having macroporous size $\beta$; and (iii) at least one support matrix chemically associated with an antigenic determinant. to form a cleansed product; wherein at least one of the hydroxyapatite, carbonaceous material and support matrix is functionalized.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Disclosed herein are compositions, processes, and devices useful in the production of a universal blood product (UBP). In an aspect the UBP is whole blood; alternatively the UBP is plasma. "Whole blood" is blood from which no constituent (e.g., plasma, platelets, or red blood cells) has been removed. Whole blood optionally includes an exogenously added anticoagulant. "Plasma" is the liquid component of whole blood in which the peripheral blood cells are suspended. Plasma is typically obtained by centrifuging whole blood to separate the plasma from the blood cells, optionally after addition of an anticoagulant. Herein, UBP refers to a universal blood product (i.e., whole blood or plasma) at least lacking anti-A antibodies (IgG) and anti-B antibodies (IgM). In an aspect of the disclosed subject matter is the preparation of a UBP having a reduced level of inflammatory molecules (e.g., cytokines) when compared to the source sample used to generate the UBP. Additional aspects of the disclosed subject matter are portable devices for the small scale production of a UBP. Yet other aspects of the disclosed subject matter are stationary devices for the large scale production of a UBP.

Aspects of the present disclosure are methods comprising introducing a blood sample comprising whole blood or blood plasma to a formulation comprising (i) hydroxyapatite; (ii) a carbonaceous material; and (iii) a support matrix chemically associated with an antigenic determinant. Such formulations are termed "cleansing formulations" as the material recovered subsequent to contact with the cleansing formulation will contain a reduced level of IgG, IgM, and inflammatory mediators. Cleansing formulation components suitable for use in the present disclosure include materials which have been subjected to a sanitization process. In an aspect, one or more of the cleansing formulation components may act as an chromatographic material. For example, one or more components of the cleansing formulation may act as an adsorbent. Herein, the term "adsorbent" is used for simplicity and it is to be understood the term "adsorbent" does not necessarily refer to the mechanism of action of the material.

Additional aspects of the present disclosure are devices containing a cleansing formulation of the type disclosed herein. It is contemplated that the cleansing formulation may be optimized for use in a particular device depending on the end-use application of the device such that the cleansing formulation suitable for a portable device may differ from the cleansing formulation suitable for a stationary device. Portable and stationary devices contemplated in aspects of the present disclosure are described independently herein.

Figure 1:
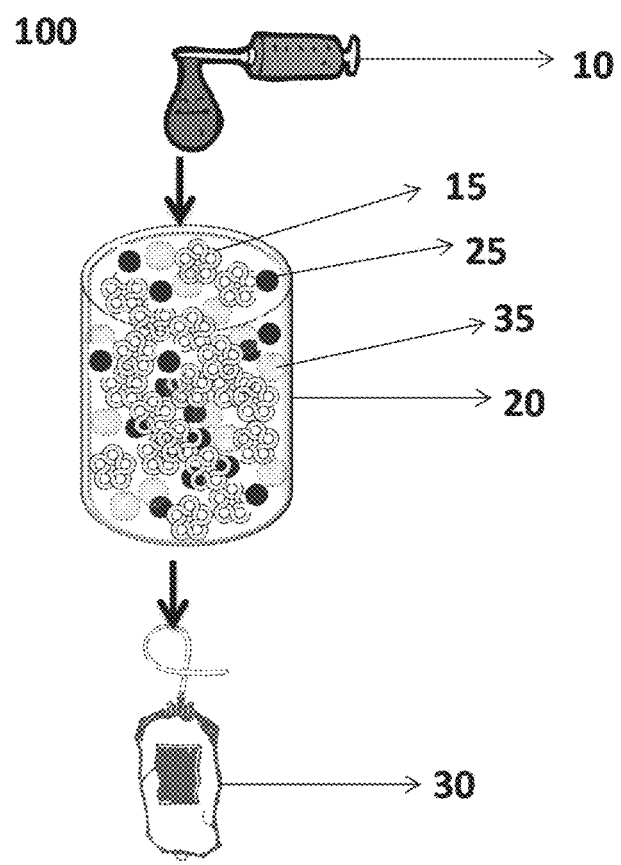
FIGS. 1 and 2 depict alternative configurations of devices of the type disclosed herein.

Referring to FIG. 1, a schematic of a methodology of this disclosure 100 comprises introducing a sample comprising either plasma or whole blood 10 to a cleansing formulation 20. The cleansing formulation 20 may be housed in a suitable vessel and may comprise (i) hydroxyapatite 15; a carbonaceous material 25; and a support matrix chemically associated with an antigenic determinant. 35. In an aspect, subsequent to contacting with the cleansing formulation 20 a universal blood product 30 is recovered and may then be administered to a subject in need thereof. The term "subject," as used herein, comprises any and all organisms and includes the term "patient."

Figure 5:
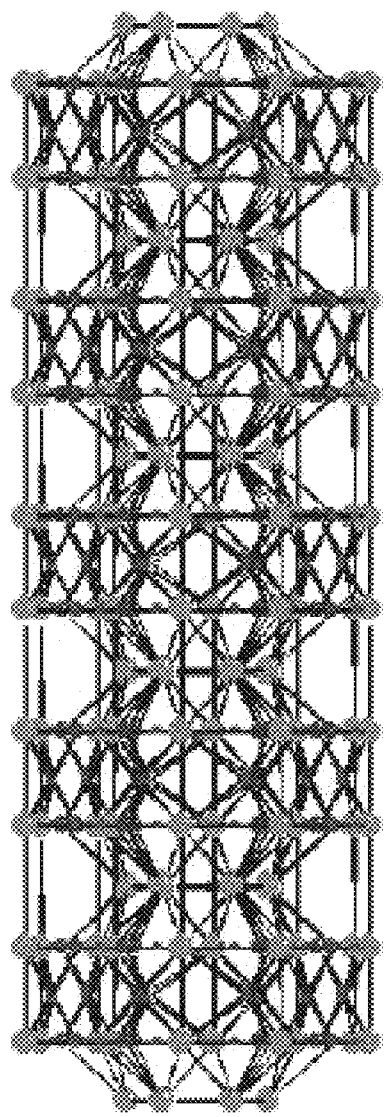
FIG. 5 depicts the hydroxyapatite crystal structure.

In an aspect, the cleansing formulation comprises hydroxyapatite. Hydroxyapatite is a naturally-occurring mineral form of calcium apatite with the formula $Ca_5(PO_4)_3(OH)$, but is usually written $Ca_{10}(PO_4)_6(OH)_2$ to denote that the crystal unit cell comprises two entities. The hydroxyapatite crystal structure is depicted in FIG. 5.

In an aspect of the present disclosure, the hydroxyapatite is a naturally-occurring material; or alternatively the hydroxyapatite is a synthetic material. In some aspects of this disclosure, the cleansing formulation comprises a combination of hydroxyapatite where at least a portion is naturally-occurring with the remainder being synthetic hydroxyapatite. A hydroxyapatite suitable for use in the present disclosure may be characterized by a pore size in the range of from about 0.2 $cm^3/g$ to about 2.0 $cm^3/g$, alternatively from about 0.5 $cm^3/g$ to about 1.5 $cm^3/g$; or alternatively from about 0.5 $cm^3/g$ to about 1.0 $cm^3/g$. The hydroxyapatite may be further characterized by a surface area ranging from about 10 $m^2/g$ to about 300 $m^2/g$, alternatively from about 50 $m^2/g$ to about 250 $m^2/g$, or alternatively from about 100 $m^2/g$ to about 200 $m^2/g$. The pore size of any material disclosed herein may be determined utilizing any suitable methodology such as by nitrogen adsorption porosimetry, for example. The surface area of any material disclosed herein may be determined utilizing any suitable methodology such as the Brunauer Emmett Teller (BET) method. For example, the surface area may be determined in accordance with ASTM D1993-91 or ASTM D6556-04.

The hydroxyapatite may be in any suitable form, for example as a granule. As used herein, "granule" means any particulate form of a substance. The term includes, therefore, powders, grains, fragments, particles, dust or the like.

In an aspect, a hydroxyapatite suitable for use in the present disclosure is ceramic hydroxyapatite. Ceramic hydroxyapatite spheres are typically manufactured by the agglomeration of small crystals (50-100 nm size range) followed by sintering at high temperature. As a result of this process, each sphere is porous and may have a mean particle size in the range of from about 1 μm to about 1000 μm, alternatively from about 10 μm to about 500 μm, or alternatively from about 100 μm to about 300 μm.

In an aspect, the cleansing formulation comprises a carbonaceous material. The carbonaceous material may be a synthetic carbon particle (SCP) containing micro-, meso- and macropores from porous phenolic resins. As used herein, the term "micropore" refers to a pores with diameter <2 nm, as measured by nitrogen adsorption and mercury porosimetry methods and as defined by IUPAC. As used herein, the term "mesopore" refers to pores with diameter from ca. 2 nm to ca. 50 nm, as measured by nitrogen adsorption and mercury porosimetry methods and as defined by IUPAC. As used herein, the term "macropore" refers to pores with diameters larger than 50 nm, as measured by nitrogen adsorption and mercury porosimetry methods and as defined by IUPAC. In relation to this invention there are two types of macropores. In macroporous beads they are located within beads and formed by pore-formers. Their size is 50-500 nm, typically 70-200 nm. These macropores are very effective in adsorption of cytokines. Typically a precursor resin formulation is used which comprises a large proportion of pore former, (e.g. 250 parts ethylene glycol or other pore former to 100 parts of resin-forming components).

Herein, a mesoporous resin may be formed by condensing a nucleophilic component which comprises a phenolic compound or a phenol condensation prepolymer with at least one electrophilic cross-linking agent selected from formaldehyde, paraformaldehyde, furfural and hexamethylene tetramine in the presence of a pore-former selected from the group consisting of a diol (e.g., ethylene glycol), a diol ether, a cyclic ester, a substituted cyclic ester, a substituted linear amide, a substituted cyclic amide, an amino alcohol and a mixture of any of the above with water to form a resin. The pore-former is present in an amount effective to impart meso- or macroporosity to the resin (e.g., at least 120 parts by weight of the pore former being used to dissolve 100 parts by weight of the total resin forming components, i.e. nucleophilic component plus electrophilic component), and it is removed from the porous resin after condensation by cascade washing with water or by vacuum drying. The resulting resin may be carbonised by heating in an inert atmosphere to a temperature of at least 600° C. to give a material having a bimodal distribution of pores, the pore structure as estimated by nitrogen adsorption porosimetry comprising micropores and mesopores or macropores. The value for the differential of pore volume with respect to the logarithm of pore radius (dV/d log R) for the mesopores is greater than 0.2 for at least some values of pore size in the range 20 Å-500 Å. The mesoporous carbon may have a BET surface area of 250 $m^2/g$-800 $m^2/g$ without activation. It may be activated by heating it at high temperature in the presence of carbon dioxide, steam or a mixture thereof, e.g. by heating it in carbon dioxide at above 800° C., or it may be activated by heating it in air at above 400° C. It may then have surface areas of up to 2000 $m^2/g$ and even higher e.g. 1000 $m^2/g$-2000 $m^2/g$.

In an aspect, the cleansing formulation comprises a support matrix chemically associated with an antigenic determinant. In such aspects, the support matrix may comprise any material capable of chemically associating with one or antigenic determinants. In an aspect, the chemical association comprises a chemical bond. In other aspects, the chemical association comprises hydrogen-bonding, van der Waals interactions, electrostatic interactions, and the like. In some aspects, the chemical association comprises a combination of chemical bonding, hydrogen-bonding, van der Waals interactions, electrostatic interactions, and the like. Additionally, the support matrix may function as a chromatographic material that aids in separation of the whole blood or plasma into constituents and/or aids in the removal of select molecules form the whole blood or plasma.

In an aspect, the support matrix comprises polyethylene (PE), sepharose; silica; polyoxymethylene (POM), polypropylene (PP), polyvinylchloride (PVC), polyvinyl acetate (PVA), polyvinylidene chloride (PVDC), polystyrene (PS), polytetrafluoroethylene (PTFE), polyacrylate, poly(methyl methacrylate) (PMMA), polyacrylamide, polyglycidyl methacrylate (PGMA), acrylonitrile butadiene styrene (ABS), polyacrylonitrile (PAN), polyester, polycarbonate, polyethylene terephthalate (PET), polyamide, polyaramide, polyethylene glycol (PEG), polyvinylpyrrolidone (PVP), polysulfone (PS), polyethersulfone (PES), polyaryletherslfone (PEAS), ethylene vinyl acetate (EVA), ethylene vinyl alcohol (EVOH), polyamide-imide, polyaryletherketone (PAEK), polybutadiene (PBD), polybutylene (PB), polybutylene terephthalate (PBT), polycaprolactone (PCL), polyhydroxyalkanoate, polyether ether ketone (PEEK), polyether ketone ketone (PEKK), polyether imide (PEI), polyimide, polylactic acid (PLA), polymethyl pentene (PMP), poly(p-phenylene ether) (PPE), polyurethane (PU), styrene acrylonitrile (SAN), polybutenoic acid, poly(4-allyl-benzoic acid), poly(glycidyl acrylate), polyglycidyl methacrylate (PGMA), poly(allyl glycidyl ether), poly(vinyl glycidyl ether), poly(vinyl glycidyl urethane), polyallylamine, polyvinylamine, copolymers of said polymers; derivatives of said polymers or combinations thereof.

In an aspect, the antigenic determinant is a blood group determinant, for example a Blood Group A antigenic determinant, a Blood Group B antigenic determinant, or a combination thereof. Any suitable Blood Group A or Blood Group B antigenic determinant may be coupled to the support matrix. In an aspect, the antigenic determinant is a trisaccharide. In an aspect, the Blood Group A antigenic determinant is the Blood Group A trisaccharide designated α-D-GalNAc-(1→3)-(α-L-Fuc-[1→2])-D-Gal and depicted in Structure 2. In an aspect, the Blood Group B antigenic determinant is the Blood Group B trisaccharide designated [Galalpha1-3(Fucalpha1-2)Gal and depicted in Structure 3.

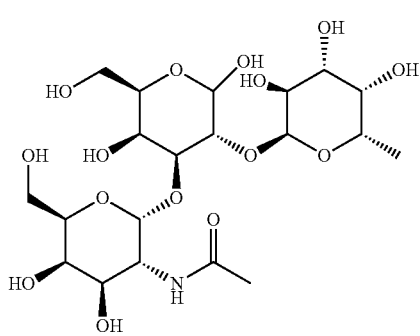

Structure 2

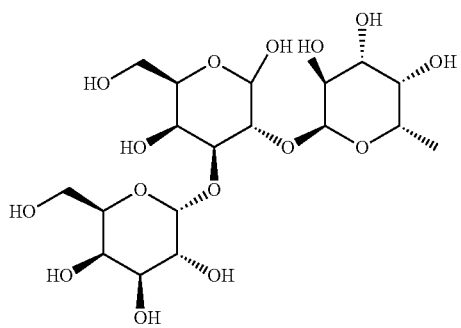

Structure 3

In some aspects, the antigenic determinants may be associated with a support matrix of the type disclosed herein using any suitable methodology. For example, the antigenic determinants may be incubated with a support matrix under conditions (e.g., temperature, time) that allow for the antigenic determinants to become chemically associated with the support matrix. In some aspects, the chemical association is permanent such that disruption of the chemical association would typically necessitate the performance of another chemical reaction to break the bond between the antigenic determinant and support matrix. In other aspects, the chemical association is transient and may persist for a period of time on the order of days, weeks or months where the chemical bond between the antigenic determinant and support matrix may be broken in the absence of performance of an additional chemical reaction.

In some aspects, any of the components of the cleansing formulation (e.g., hydroxyapatite, carbonaceous material, support matrix with chemically associated antigenic determinant) may be functionalized with one or more moieties to selectively enhance the affinity of the material for molecules to be removed from the whole blood or plasma. For example, the cleansing formulation component may be hydroxyapatite functionalized with one or more amino acids.

In an aspect of the present disclosure, molecules (e.g., antibodies raised against anti-A, anti-B, anti-antibodies, anti-cytokines and the like, and or synthetic ligands) may be chemically associated with one or more of the cleansing formulation components via a chemical reaction to link said molecule with the cleansing formulation component. For example, such molecules may be attached to a polyvinylamine/polysulfone composite hollow-fiber or membrane via a Schiff reaction-based on a glutaraldehyde cross-linking method. In an alternative aspect of the present disclosure, one or molecules of interest (e.g., antibodies raised against anti-A, anti-B, anti-antibodies, anti-cytokines and the like, and or synthetic ligands) may be aldehyde activated by an oxidizing agent (e.g., sodium meta-periodate) to generate functional moieties capable of reacting with (e.g., binding) one or more molecules of interest. An example of this type of reaction is schematized below.

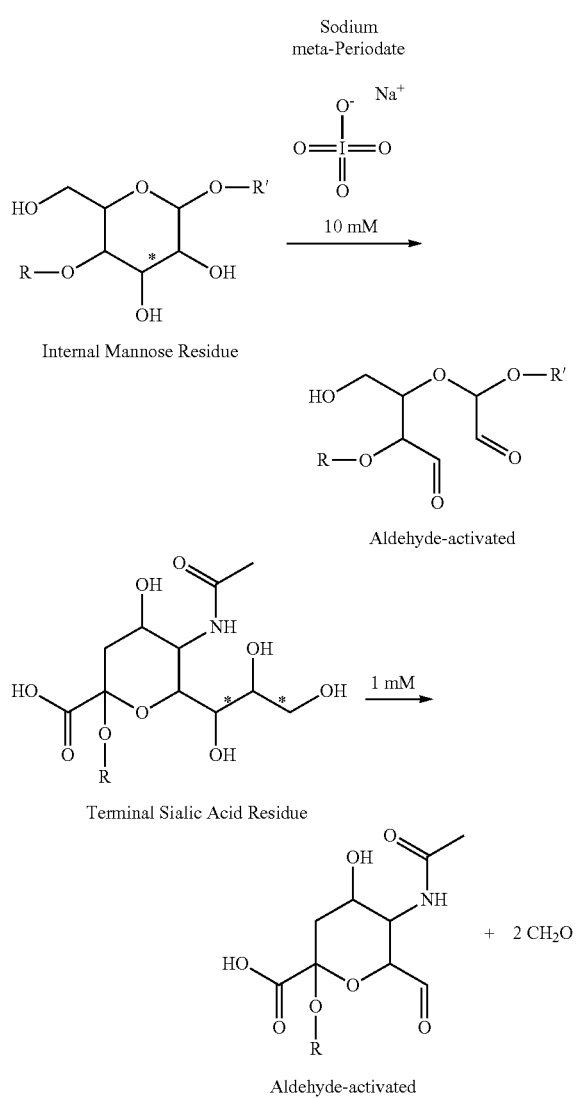

In an aspect, a support matrix and an antigenic determinant, both of the type disclosed herein may be functionalized to introduce reactive sites into these materials. In an aspect, a support matrix chemically associated with an antigenic determinant is formed as a construct designate M-L-A where M denotes the support matrix, L denotes a linker agent, and A denotes an antigenic determinant. M and A are disclosed independently herein. In an aspect, L may be any compound able to concurrently bond to both the support matrix and antigenic determinant thus forming a bridge between the molecules. For example, L may be an amino acid or peptide; alternatively an amino acid comprising at least two amine groups such as lysine. In an aspect oxidation of the support matrix and antigenic determinant results in the formation of aldehyde bonds which react with a linker agent (e.g., L-lysine) to couple the antigenic determinant to the support matrix via an L-lysine linker agent.

In an aspect, an antigenic determinant (e.g., A-trisaccharide) is covalently immobilized on a substrate (e.g., polyvinyl alcohol beads) subsequent to oxidation (e.g., via contact with periodate) of both the substrate and antigenic determinant. A linker agent (L-lysine) may complex with the free amine groups reactive with the aldehyde groups present on both the oxidized PVA and the antigenic determinant to form a carbonyl bonds which is reduced by reaction with a reducing agent (e.g., sodium borohydride).

It is contemplated that other methodologies for functionalization of the materials disclosed herein may be carried out in order to improve the efficiency with which the cleansing formulation removes one or more molecules and/or to alter the cleansing formulation for use in particular applications.

In an aspect, any or all of the cleansing formulation components (e.g., hydroxyapatite, carbonaceous material, support matrix with chemically associated antigenic determinant) may be subjected to a sanitization process prior contacting whole blood or plasma. Herein, the sanitization process refers to a method of treating the cleansing formulation components (CFC) in order to (i) remove pathogens; (ii) reduce the amount of fine particulates and leachables; (iii) reduce the amount of trapped air and (iv) sterilize the materials. CFCs that have been subjected to the sanitization process disclosed herein are considered to have been converted from an industrial grade material to a pharmaceutical grade material with a concomitant increase in hemocompatability.

In an aspect, a method for sanitization of a CFC comprises a dry heat treatment. Dry heat treatment of the CFC may be carried out at a temperature equal to or greater than about 180° C. for a time period equal to or greater than about 4 hours, alternatively at a temperature of equal to or greater than about 200° C. for a time period of equal to or greater than about 1 hour, or alternatively at a temperature of 250° C. for a time period of equal to or greater than about 30 min. Dry heat treatment of the CFC may function to reduce the bioburden of the material and particularly the amount of pathogenic (e.g., bacteria, viruses, fungi, etc.) and pyrogenic (e.g., endotoxin) substances associated with the CFC. For example, the total amount of pathogenic substances associated with the heat-treated CFC may be reduced by greater than about 50%, alternatively greater than about 90%, alternatively greater than about 91%, alternatively greater than about 92%, alternatively greater than about 93%, alternatively greater than about 94%, alternatively greater than about 95%, alternatively greater than about 96%, alternatively greater than about 97%, alternatively greater than about 98%, alternatively greater than about 99%, or alternatively about 100% when compared to the amount present in the CFC prior to heat treatment.

In an aspect, the bioburden of the CFC is reduced by about 100% through the use of a dry heat treatment. Alternatively, the bioburden of the CFC is reduced through the use of any suitable methodology compatible with the CFC and the other aspects of the present disclosure. In some aspects, the bioburden of the CFC is reduced by 100% utilizing methodologies consistent with jurisdictional guidelines for the sanitization of materials that will contact mammalian blood and produce a product that will be subsequently utilized in mammals.

In an aspect, a method for sanitization further comprises the removal of fine particulates and leachables from the heat-treated CFC. Herein, particulates smaller than about 30 microns are referred to as "fines" while "leachables" describe the organic compounds that can be eluted from the cleansing formulation in the presence/absence of an applied sample. In an aspect, removal of the fine particulates and leachables from the heat-treated CFC comprises contacting the heat-treated CFC with water, removing water from the heat-treated CFC to produce a washed CFC, contacting the washed CFC with a salt solution to produce a modified CFC, and removing the salt solution from the modified CFC to produce a processed CFC. The heat-treated CFC may be contacted with from about 4 volumes to about 10 volumes of water, alternatively from about 5 volumes to about 10 volumes of water or alternatively from about 6 volumes to about 8 volumes of water. Contacting of the CFC with a substance may be carried out in any suitable vessel. For example, the CFC may be positioned within a cartridge or column to facilitate contacting with one or more substances of the type disclosed herein. For example, the washed CFC may be contacted with a solution comprising sodium chloride salt at a concentration of 3 g/dL. The washed CFC may be contacted with from about 4 volumes to about 10 volumes of salt solution based on the total volume of the CFC, alternatively from about 6 volumes to about 10 volumes of salt solution or alternatively from about 6 volumes to about 8 volumes of salt solution. It is contemplated that other salt solutions providing similar pH and osmolarity, such as known to the ordinarily skilled artisan and compatible with the other methods and compositions of the present disclosure, may be employed to facilitate the removal of fine particulates and leachables from the CFC.

For either the removal of water to produce a washed CFC or the removal of salt to produce a processed CFC, the removal may be effected using any suitable methodology. For example, the removal of fine particulates and leachables may be carried out by placing the CFCs in a column which may be allowed to drain under gravity until no further filtrate is detected. In some aspects, the CFCs may be subjected to a plurality of processes for the removal of fine particulates and leachables. Further, in some aspects, the solution produced by contacting the CFCs with water and/or a salt solution may be analyzed to determine the amount of fine particulates and/or leachables removed following contact. Such determinations may be made and the process for removal of fine particulates and/or leachables repeated until some user and/or process desired level of fine particulates and/or leachables is achieved.

In an aspect, a method for sanitization further comprises dewatering the processed CFC. Water present with the CFCs has the tendency to separate from the material resulting in compaction and a reduction in flow properties. De-watering is the process of removing extraneous fluid (typically water or aqueous solutions) from wet or slurried particles without removing fluid in the particles (i.e., prevent evaporative drying of the particles). Herein, "extraneous" means any fluid outside the particles. Therefore any fluid absorbed into the polymer matrix or present in the pores is not considered extraneous.

Any suitable methodology may be employed for the dewatering of the processed CFC. Examples of methodologies suitable for use in dewatering the processed CFC include without limitation the passage of air through the particles. The resultant material is referred to as the dewatered CFC. In an aspect, dewatering of the processed CFC is carried out using a dewatering apparatus.

In an aspect, a method for sanitization further comprises aseptic processing of the dewatered CFC, also referred to as sterile fill and sterilization to produce a sanitized CFC. Sterility may be achieved using any suitable methodology. For example, sterile processing may include the use of clean rooms, bacteria-retaining filters, and dry or steam heat. In an aspect, aseptic processing of the dewatered CFC comprises terminal sterilization by autoclaving (e.g., at 121° C., 15 psi for 30 min), gas sterilization, e-beam sterilization, gamma radiation, or combinations thereof.

In an aspect, any of the CFCs may be contacted with a compatibilizer which functions to coat at least a portion of the surface area of the CFC. Herein, a compatibilizer refers to a substance that functions to increase the biocompatibility of the CFC with biological fluids (e.g., plasma) and may aid in decreasing the binding of non-target molecules to the CFC. In an aspect, the compatibilizer comprises a polysaccharide, a glucan, albumin, mannitol, a starch, or combinations thereof.

In an aspect, the compatibilizer comprises dextran. Dextrans, representations are depicted in Formula 1, are polysaccharides having a linear backbone of α-linked D-glucopyranosyl repeating units. In an aspect, a dextran suitable for use in the present disclosure has an average molecular weight ranging from about 1 kDa to about 500 kDa, alternatively from about 1 kDa to about 70 kDa, alternatively from about 1 kDa to about 40 kDa, or alternatively from about 40 kDa to about 70 kDa. Nonlimiting examples of compatibilizers suitable for use in the present disclosure include DEXTRAN-1, DEXTRAN-40 and DEXTRAN-70 commercially available from Hospira Inc.

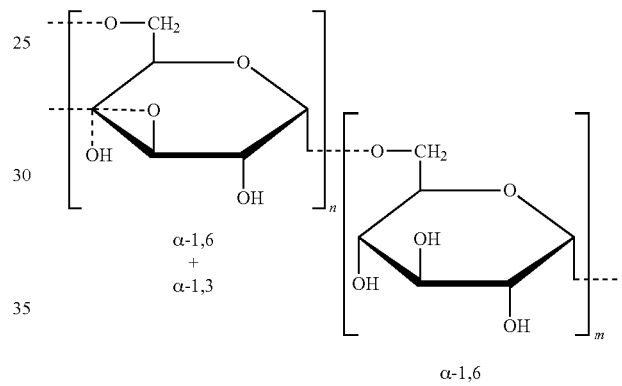

Formula I

In an aspect, the compatibilizer comprises hydroxyethyl starch. Hydroxyethyl starch, depicted in Formula II, is a nonionic starch derivative that is commonly used as a volume expander in a type of intravenous therapy that has the function of providing volume for the circulatory system.

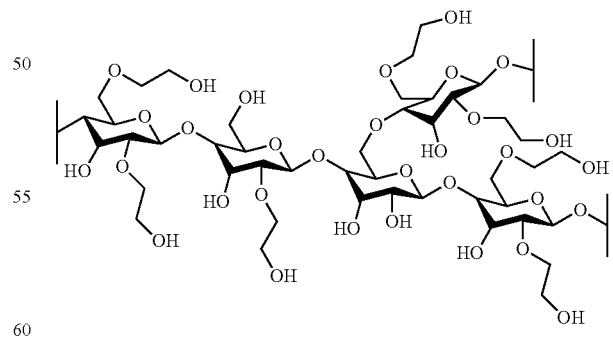

Formula II

In an aspect, the compatiblizer comprises a mixture of albumin and mannitol. Serum albumin is the main protein of human blood plasma whose primary function is to regulate the colloidal osmotic pressure of blood. Mannitol, (2R,3R,4R,5R)-Hexan-1,2,3,4,5,6-hexol, is a sugar alcohol, which can function an Osmotic Diuretic. The weight ratio of albumin to mannitol in the compatibilizer may range from 20:1 to 1:1, alternatively from 18:1 to 1:1, or alternatively from 15:1 to 10:1.

Without wishing to be limited by theory, the compatibilizer (e.g., dextran) may function to prime the device (i.e., apparatus having columns containing the cleansing formulation) and may lessen complications by blocking the initial exposure of blood components and plasma to foreign surfaces while maintaining a higher level of colloid osmotic pressure. In an aspect, the compatibilizer is dextran 40 which may function in (i) preventing shear-induced fines formation via a lubrication effect; (ii) serving as a priming agent to prevent activation of plasma and other blood components following early primary exposure; and (iii) modulating sorbing capacity of porous sorbents such as synthetic mesoporous/microporous carbon. For example, the CFCs packed into columns as components of an apparatus of the type disclosed herein, during storage/distribution can be exposed to relatively high shear stresses which can be a continuous source of particulates while dextran may prevent fines formation by lubrication at any shear condition.

CFCs suitable for use in the present disclosure may be contacted with the compatibilizer using any suitable methodology. In an aspect, the compatibilizer is dextran which may be formulated as a solution suitable for use in the present disclosure having from about 1 weight percent (wt. %) dextran about 10 wt. % dextran, alternatively from about 2 wt. % to about 9 wt. % or alternatively from about 3 wt. % to about 7 wt. %. In an aspect, the compatibilizer is hydroxyethyl starch which may be formulated as a solution suitable for use in the present disclosure having from about 1 wt. % to about 6 wt. % hydroxyethyl starch, alternatively from about 1.5 wt. % to about 6 wt. % hydroxyethyl starch or alternatively from about 2 wt. % to about 6 wt. % hydroxyethyl starch. The resultant compatibilized CFC may be characterized by the formation of a coating of the compatibilizer on the particles of the CFC such that the coating covers greater than about 50% of the particle's surface; alternatively, greater than about 60%, 70%, 80% or 90% of the particle's surface.

In an aspect, the CFCs are present in any amount suitable to effectively carry out a particular application such as, for example, the conversion of a sample of plasma isolated from an unknown subject to a UBP. Thus, the ratio of hydroxyapatite:carbonaceous material:support matrix chemically associated with an antigenic determinant may range from 1:1000:1000 to 1000:1:1, alternatively from 10:100:500 to 500:100:10, alternatively from 100:10:500 to 500:10:100, alternatively from 0.1:1:10 to 10:1:0.1: or alternatively from 1:1:1.

In an aspect, the whole blood or plasma contacted with a cleansing formulation of the type disclosed herein may be obtained from a single subject. In an alternative aspect, the whole blood or plasma contacted with a cleansing formulation of the type disclosed herein may be obtained from a plurality of subjects such as two or more subjects, or ten or more subjects, or twenty or more subjects. Such samples may be collected and/or stored using any suitable methodology for collection and/or storage of whole blood or plasma.

Figure 2:
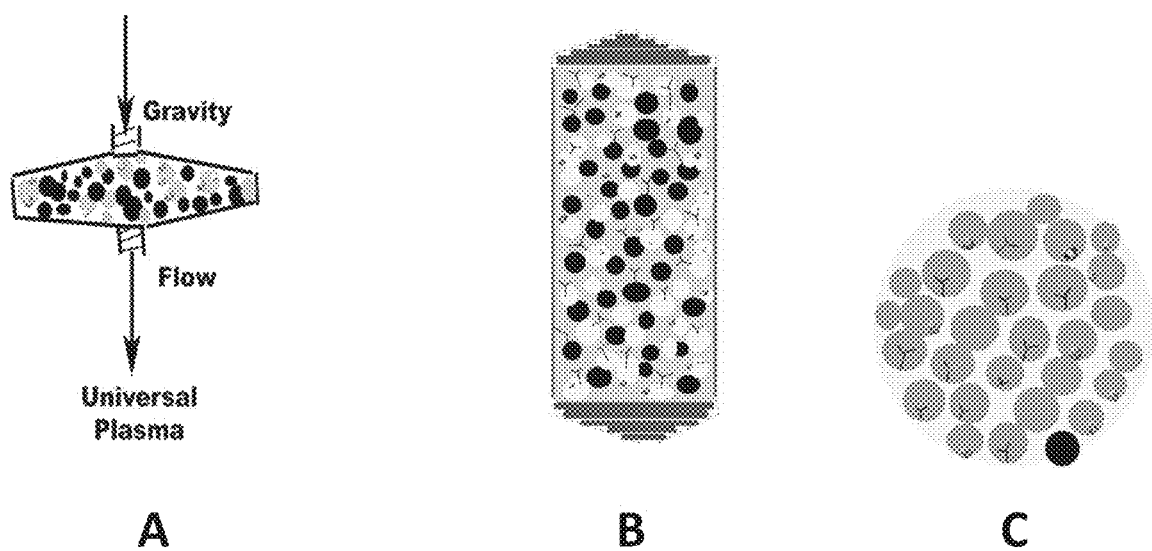

In an aspect, a sample (e.g., whole blood or plasma) is contacted with a cleansing formulation of the type disclosed herein that is a component of an extracorporeal device. Aspects of devices suitable for use in the present disclosure are depicted in FIG. 2. For example, FIG. 2A discloses a device scaled suitably to be portable. Such a device may be portable (e.g., handheld) and may be utilized for the generation of a UBP using a sample obtained from a single subject (i.e., is a personal device). The device containing the cleansing formulation may be used at the point of sample collection and UBP transfusion, driven via gravity alone, on an individual subject.

In another aspect, FIG. 2B, a column containing a cleansing formulation of the type disclosed herein may be suitably scaled to be a component of a stationary apparatus for the generation of a UBP using a sample obtained from a plurality of subjects.

In yet another aspect, FIG. 2C, a hollow fiber system having a cleansing formulation chemically associated with the system may be used as a component of an apparatus to perform pooled plasma cleansing in a large volume that is driven at a high flow rate.

Figure 3:
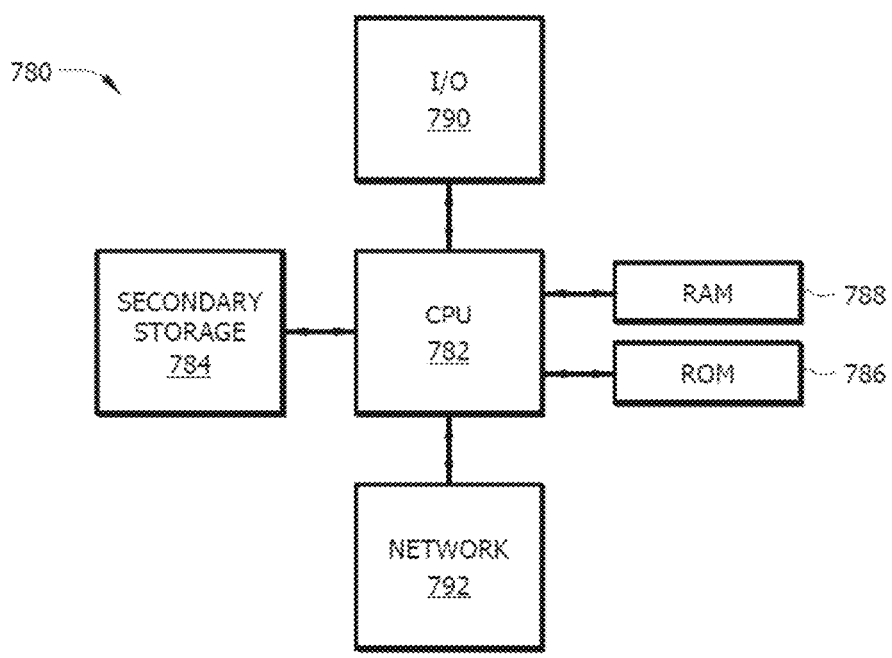
FIG. 3 depicts a system of the type disclosed herein.

Any aspect or aspect may be carried out manually. In the alternative, one or more aspects disclosed herein may be automated. FIG. 3 illustrates a computer system 780 suitable for implementing one or more aspects disclosed herein. The computer system 780 includes a processor 782 (which may be referred to as a central processor unit or CPU) that is in communication with memory devices including secondary storage 784, read only memory (ROM) 786, random access memory (RAM) 788, input/output (I/O) devices 790, and network connectivity devices 792. The processor 782 may be implemented as one or more CPU chips.

It is understood that by programming and/or loading executable instructions onto the computer system 780, at least one of the CPU 782, the RAM 788, and the ROM 786 are changed, transforming the computer system 780 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 784 is typically comprised of one or more disk drives or tape drives and is used for non-volatile storage of data and as an over-flow data storage device if RAM 788 is not large enough to hold all working data. Secondary storage 784 may be used to store programs which are loaded into RAM 788 when such programs are selected for execution. The ROM 786 is used to store instructions and perhaps data which are read during program execution. ROM 786 is a non-volatile memory device which typically has a small memory capacity relative to the larger memory capacity of secondary storage 784. The RAM 788 is used to store volatile data and perhaps to store instructions. Access to both ROM 786 and RAM 788 is typically faster than to secondary storage 784. The secondary storage 784, the RAM 788, and/or the ROM 786 may be referred to in some contexts as computer readable storage media and/or non-transitory computer readable media.

I/O devices 790 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 792 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 792 may enable the processor 782 to communicate with an Internet or one or more intranets. With such a network connection, it is contemplated that the processor 782 might receive information from the network, or might output information to the network in the course of performing the above-described method steps. Such information, which is often represented as a sequence of instructions to be executed using processor 782, may be received from and outputted to the network, for example, in the form of a computer data signal embodied in a carrier wave.

Such information, which may include data or instructions to be executed using processor 782 for example, may be received from and outputted to the network, for example, in the form of a computer data baseband signal or signal embodied in a carrier wave. The baseband signal or signal embodied in the carrier wave generated by the network connectivity devices 792 may propagate in or on the surface of electrical conductors, in coaxial cables, in waveguides, in an optical conduit, for example an optical fiber, or in the air or free space. The information contained in the baseband signal or signal embedded in the carrier wave may be ordered according to different sequences, as may be desirable for either processing or generating the information or transmitting or receiving the information. The baseband signal or signal embedded in the carrier wave, or other types of signals currently used or hereafter developed, may be generated according to several methods well known to one skilled in the art. The baseband signal and/or signal embedded in the carrier wave may be referred to in some contexts as a transitory signal.

The processor 782 executes instructions, codes, computer programs, scripts which it accesses from hard disk, floppy disk, optical disk (these various disk based systems may all be considered secondary storage 784), ROM 786, RAM 788, or the network connectivity devices 792. While only one processor 782 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 784, for example, hard drives, floppy disks, optical disks, and/or other device, the ROM 786, and/or the RAM 788 may be referred to in some contexts as non-transitory instructions and/or non-transitory information.

In an aspect, the computer system 780 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an aspect, virtualization software may be employed by the computer system 780 to provide the functionality of a number of servers that is not directly bound to the number of computers in the computer system 780. For example, virtualization software may provide twenty virtual servers on four physical computers. In an aspect, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an aspect, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 780, at least portions of the contents of the computer program product to the secondary storage 784, to the ROM 786, to the RAM 788, and/or to other non-volatile memory and volatile memory of the computer system 780. The processor 782 may process the executable instructions and/or data structures in part by directly accessing the computer program product, for example by reading from a CD-ROM disk inserted into a disk drive peripheral of the computer system 780. Alternatively, the processor 782 may process the executable instructions and/or data structures by remotely accessing the computer program product, for example by downloading the executable instructions and/or data structures from a remote server through the network connectivity devices 792. The computer program product may comprise instructions that promote the loading and/or copying of data, data structures, files, and/or executable instructions to the secondary storage 784, to the ROM 786, to the RAM 788, and/or to other non-volatile memory and volatile memory of the computer system 780.

In some contexts, a baseband signal and/or a signal embodied in a carrier wave may be referred to as a transitory signal. In some contexts, the secondary storage 784, the ROM 786, and the RAM 788 may be referred to as a non-transitory computer readable medium or a computer readable storage media. A dynamic RAM aspect of the RAM 788, likewise, may be referred to as a non-transitory computer readable medium in that while the dynamic RAM receives electrical power and is operated in accordance with its design, for example during a period of time during which the computer 780 is turned on and operational, the dynamic RAM stores information that is written to it. Similarly, the processor 782 may comprise an internal RAM, an internal ROM, a cache memory, and/or other internal non-transitory storage blocks, sections, or components that may be referred to in some contexts as non-transitory computer readable media or computer readable storage media.

In one or more aspects of the present disclosure, the cleansing formulations disclosed herein can be used at the point of plasma collection or transfusion, and is a component of a device that is driven by gravity alone. Further advantages of the presently disclosed cleansing formulations are absence of biologics, antibodies or ligands that can leach or degrade over time, and a shelf life at ambient temperature of more than 2 years. In some aspects, a handheld device of the type disclosed herein is a component of a military personnel's standard issued gear and is storable in areas such as a rucksack. In an alternative aspect, the cleansing formulation is a component of a stationary device for use in high throughput generation of UBP using sample obtained from more than one subject.

In an aspect, the cleansing formulation may be functionalized with one or more moieties to enhance the affinity of the material for association with IgG and/or IgM. In an aspect, the cleansing formulation is hydroxyapatite and is functionalized with one or more amino acids. Hydroxyapatite suitable for use in the present disclosure may assume any appropriate form. For example, the hydroxyapatite may be nanoparticles, beads, or granules. Disclosed herein is a method comprising exposure of plasma obtained from an individual containing disease mediators such as anti-A and anti B antibodies, other autoantibodies and disease molecules, and contacting with an cleansing formulation comprising an activated carbon bead and large porous adsorbent supported by synthetic ligands to produce an eluent free of these mediators, which can be administered to said subject.

In an aspect, the compositions and methods disclosed herein are utilized in the treatment of one or more medical conditions. In an aspect, the medical condition is selected from the group consisting of metabolic disorders, inflammatory diseases, degenerative diseases, neoplastic diseases, and systemic immune response (SIRS) disorders or SIRS-like disorders and the bodily fluid is plasma with blood cellular components. Herein inflammatory diseases refer to those in which the body reacts to an injurious agent by means of inflammation. Herein degenerative diseases refer to diseases where the primary abnormality is degeneration of a part of the body. Herein metabolic diseases refer to those where the primary abnormality is a disturbance in an important metabolic process in the body. Herein neoplastic disease refers to a disease where the primary abnormality is unregulated cell growth leading to the formation of various types of benign and malignant tumors. Hereinafter for simplicity, medical conditions selected from the group consisting of metabolic disorders, inflammatory diseases, degenerative diseases, neoplastic diseases and SIRS or SIRS-like disorders are collectively termed Class A disorders.

In an aspect, the medical condition is a neoplastic disorder such as cancer. Cancer is a major public health problem in the United States and many other parts of the world. In 2013, in the United States alone, there were 1,660,290 new occurrences. Cancer is the second most common cause of mortality. The most prevalent symptom that patients with cancer experience is cancer-related fatigue, which is pervasive and affects patients' quality of life and productivity. Anemia and cachexia, contribute to fatigue, lethargy, tiredness, or lack of energy. Pro-inflammatory factors are implicated in many of the mechanisms proposed for the etiology of comorbidities seen in cancer, as well as cancer promotion and progression. Chronic inflammation can be oncogenic by various mechanisms: (i) induction of genomic instability, (ii) increasing angiogenesis, (iii) altering the genomic epigenetic state and (iv) increasing cell proliferation, Chronic inflammation also induces anemia and cachexia observed in cancer. Key molecular factors that contribute to inflammation-induced carcinogenic events are: (i) over-production of reactive oxygen and nitrogen species (RNOS), (ii) activation of nuclear factor (NF)-kappa B, (iii) massive expression of inflammatory cytokines and chemokines, and (iv) increased cyclooxygenase-2 activity. Pro-inflammatory cytokines and growth factors expressed in excess in cancer have a negative impact on: (i) erythropoiesis, leading to anemia (TNF-α, IL-1β, IL-13, TGF-β1), (ii) angiogenesis that facilitates tumor growth (VEGF, EGF, βFGF), (iii) tumor progression and metastasis (TNF-α, IL-Iβ, IL-6, IL-8), as well as (iv) cachexia (TNF-α, IL-6, IFN-γ) and other comorbidities.

In an aspect, the medical condition is a metabolic disorder resulting in chronic kidney disease (CKD). CKD is defined as kidney damage or a glomerular filtration rate (GFR) below 60 and is a result of metabolic syndrome. GFR is a measure of the level of kidney function. CKD affects 20 million Americans (1 in 9 adults) and another 20 million are at increased risk. Hemodialysis does not stop progression to end-stage and patients are at high risk for developing anemia and other comorbidities. Early treatment of anemia is recommended to minimize the symptoms and improve quality of life. The treatment is difficult, since anemia in CKD is mainly not erythropoietin (EPO) deficient. In fact, CKD patients suffer from significantly higher oxidative stress and systemic inflammation. EPO and TGF-β1 levels are about 3 times those of the controls. High TGF-β1 levels prevent erythropoiesis. TNF-α, IL-1β and IFN-γ, which showed to be strong anti-erythropoietic agents, are also elevated. While inflammatory cytokines (TNF-α, IL-1β, IL-6, IL-8, IFN-γ) accelerate the progression of kidney disease and its subsequent cardiovascular complications, the TGF-β superfamily, besides CKD anemia, mediates nephrosclerosis. Other nephrotoxic molecules include uric acid, free hemoglobin, CRP, and active lipid- (i.e., 8-isoprostane), oxygen- and nitrogen-species.

In an aspect, the medical condition is a degenerative disorder such as cardiovascular disease and the bodily fluid is plasma with blood cellular components. Cardiovascular diseases are the leading cause of death in the United States. They kill an estimated 17 million people worldwide each year. Cardiovascular diseases are a group of disorders of the heart and blood vessels and include: (i) coronary heart disease, (ii) cerebrovascular disease, (iii) peripheral arterial disease, (iv) rheumatic heart disease, (v) congenital heart disease, (vi) deep vein thrombosis and (vii) pulmonary embolism. Heart attacks and strokes are caused by a blockage that prevents blood from flowing to the heart or brain. The most common reason is atherosclerosis, formerly considered only as a bland lipid storage disease, but actually involves an ongoing inflammatory response. The mediators of cardiovascular diseases include: cholesterol, triglyceride, LDL, VLDL, ox-LDL, other biologically active lipids and pro-inflammatory mediators such as C-reactive protein (CRP) and cytokines. In the early stages, cardiovascular disease may be treated by lifestyle modifications aimed at slowing or stopping its progression. In advanced stages, surgical intervention or a non-surgical procedure may be necessary.

In an aspect, the medical condition is a SIRS or SIRS-like disorder and the bodily fluid is plasma with blood cellular components. Very often neoplastic, renal and cardiovascular events driven by inflammatory responses can lead to the devastating and difficult to treat the Systemic Inflammatory Response Syndrome (SIRS). In fact, sepsis has a high mortality rate at approximately 25-50%. Septic shock is characterized by hypotension, defective $O_2$ binding, lactic acidemia and myocardial depression. These pathological responses are mediated by circulating endotoxin (LPS) that activates phagocytes to release TNF-α which in turn activates NOS converting L-arginine to NO. NO stimulates production of cGMP that lowers intracellular calcium resulting in hypotension and myocardial depression. Acute respiratory distress syndrome (ARDS), commonly observed in septic shock, results in lactic acidosis that lowers Hb oxygen affinity, thus deepening hypoxia that leads to multi organ failure (MOF). SIRS is a medical emergency. The treatment is difficult, since it involves the overproduction of inflammatory mediators as a consequence of the interaction of the immune system with endotoxin constituents in the body.

SIRS is a common complication in other medical conditions that has a high mortality rate, particularly burns. According to CDC deaths from fires and burns are the third leading cause of fatal home injury. On average in the United States, someone dies in a fire every 169 minutes, and someone is injured every 30 minutes. Fire and burn injuries represent 1% of the incidence of injuries and 2% of the total costs of injuries, or $7.5 billion each year. Burn injuries are characterized by (i) endotoxemia that results from bacterial translocation and leads to hypotension and end organ hypoperfusion, (ii) oxidative stress, (iii) SIRS, (iv) capillary leak syndrome (CLS), (v) hypoalbuminemia and (vi) immunosuppression with depressed T-cell function that results in infections. These pathological responses are mediated by circulating endotoxin that activates phagocytes to release TNF-α that in turn activates NOS converting L-arginine to NO. NO stimulates production of cGMP that lowers intracellular calcium producing hypotension and myocardial depression. Acute respiratory distress syndrome (ARDS) is also commonly observed in burns. Increased production of inflammatory cytokines (TNF-α, IL-1, IL-6, IL-8) lead to SIRS. TGF-β1, IL-10 and NO are immunosuppressive. Activated alternative pathway of complement participates in CLS. Burn is a medical emergency. The treatment of burns is a complex problem, since it involves the overproduction of inflammatory and other mediators with associated immunosuppression that complicates the treatment. *P. aeruginosa* infections are particularly opportunistic in burns.

These medical conditions can lead to the dysfunction of organs and accumulation of toxic metabolites. Hepatic encephalopathy (HE), which accompanies many disease states such as neoplastic, metabolic, traumatic, infectious, and toxicosis, is a condition with significant morbidity and mortality. HE is caused by an accumulation of circulating toxins that are damaging to CNS, particularly ammonia ($NH_3$), marcaptans and phenol, normally removed by the liver. Chronic liver failure and pancreatic patients also suffer from bilirubinemia resulting in jaundice and at higher levels is neurotoxic.

In an aspect, the medical condition is the ingestion of poisons and/or drugs at levels that are harmful to the body and the bodily fluid is plasma with blood cellular components. Herein for simplicity, a medical condition arising from the ingestion of poisons and/or drugs at high level are termed Class B conditions. Every day in the United States, 120 people die as a result of drug overdose, and another 7,000 are treated for the misuse or abuse of drugs. Nearly 9 out of 10 poisoning deaths are caused by drugs. In 2013, of the 43,982 drug overdose deaths in the United States, 22,767 (51.8%) were related to pharmaceuticals. Of the 22,767 deaths relating to pharmaceutical overdose in 2013, 16,235 (71.3%) involved opioid analgesics and 6,973 (30.6%) involved benzodiazepines. People who died of drug overdoses often had a combination of benzodiazepines and opioid analgesics in their bodies. The most common drugs toxicities involve acetaminophen, anticholinergic drugs, which block the action of the neurotransmitter acetylcholine (such as atropine, scopolamine, belladonna, antihistamines, and antipsychotic agents), antidepressant drugs such as amitriptyline, desipramine, and nortriptyline); cholinergic drugs, which stimulate the parasympathetic nervous system (carbamate, pilocarpine, etc.); cocaine and crack cocaine; depressant drugs (tranquilizers, antianxiety drugs, sleeping pills); digoxin, a drug used to regulate the heart; narcotics or opiates (heroin, morphine, codeine, etc.), salicylates (aspirin) and many others.

In any aspect wherein the compositions and methodologies are utilized in the treatment of a medical condition, other treatments (e.g., conventional therapies) may be utilized in conjunction with the disclosed subject matter.

Also disclosed herein is a method comprising exposure of pooled plasma obtained from many individuals, containing disease mediators such as anti-A and anti B antibodies, other autoantibodies and disease molecules, and contacting with an cleansing formulation comprising an activated carbon bead, large porous adsorbent, anionic resin, cationic resin, PVA beads, PSF membranes with immobilized PEG, EVAL membranes, styrene DVB beads, supported by antibodies, amino acids (tryptophan, phenylalanine, histidine, serine and the like) and synthetic ligands to produce an eluent free of these mediators, which can be administered to said subjects.

Also disclosed herein is a method comprising exposure of pooled plasma obtained from many individuals, containing disease mediators such as anti-A and anti B antibodies, other autoantibodies and disease molecules, and contacting with hollow fibers and or membranes with incorporated antibodies and synthetic ligands to produce an eluent free of these mediators, which can be administered to said subjects.

Also disclosed herein is a personal device filled with cleansing formulations used at the point of plasma collection and transfusion, driven via gravity alone, on an individual subject Also disclosed herein is a system comprising group of devices filled with one or more cleansing formulations, supported by antibodies and/or synthetic ligands to perform pooled plasma cleansing in a large volume, driven under pressure.

Also disclosed herein is a hollow fiber system with attached antibodies and/or synthetic ligands to perform pooled plasma cleansing in a large volume, driven at a high flow rate.

Also disclosed herein is a synthetic carbon material with bead sizes between 125 and 500 um and porosity between 2 and 200 nm. Also disclosed herein is a method for chemical activation of PVDF hollow fibers and membranes (polyvinylidene fluoride matrix) to incorporate antibodies raised against target molecules, particularly anti-A, anti-B, anti-antibodies, anti-cytokines, and the like, and or synthetic ligands.

Also disclosed herein is a method for incorporation of antibodies raised against anti-A, anti-B, anti-antibodies, anti-cytokines and the like, and or synthetic ligands into polyvinylamine/polysulfone composite hollow-fibers or membranes, via a Schiff reaction-based on glutaraldehyde cross-linking method.

Also disclosed herein is a method for chemical activation of hollow fibers and membranes with poly(vinyl alcohol) (PVA) via sodium periodate ($NaIO_4$) to create aldehyde groups reactive with antibodies raised against target molecules, particularly anti-A, anti-B, antiantibodies, anti-cytokines, and the like, and or synthetic ligands.

EXAMPLES

The subject matter of the present disclosure having been generally described, the following examples are given as particular aspects of the disclosure and to demonstrate the practice and advantages thereof. It is understood that the examples are given by way of illustration and are not intended to limit the specification or the claims to follow in any manner.

Example 1

Immobilization of Synthetic Blood Group Trisaccharides that Serve as Ligands for Anti-A and Anti-B Antibodies into Microporous/Mesoporous Synthetic Carbon Beads. Microporous/Mesoporous/Macroporous Hydroxyapatite and PVA Beads.

Synthetic carbon in two beads size was use to prepare a carbonaceous material of the type disclosed herein having a porosity permitting adsorption of molecules similar in mass to IgG (approx. 160 kDa). Hydroxyapatite with a larger porosity is able to accept large molecules such as IgM (approx. 950 kDa). These materials have a proven high biocompatibility with human blood and individual efficacy toward IgG and IgM removal. To add affinity forces toward anti-A and anti-B antibodies, these adsorbents were immobilized with A- and B-trisaccharides. Without wishing to be limited by the theory, the combining two forces: adsorption and affinity accelerated the removal of anti-A and anti-B antibodies.

The saccharides mimicking A and B blood group antigens: blood group A-trisaccharides [Ga1NAcalpha1-3(Fucalpha1-2)Ga1 and blood group B-trisaccharides [Galalpha1-3(Fucalpha1-2)Ga1 (Sigma Aldrich, St. Louis, Mo.), were incubated with: —microporous/mesoporous synthetic carbon beads, and —hydroxyapatite beads. Materials were incubated at 37° C. while mixing (45° C., 60 cycles/min, Aliquot Mixer, Model 4561, Ames Company, Ames, Iowa). Samples were collected at 0, 1, and 4 hr intervals. Supernates containing free A and B trisaccharides were screened with the ELISA method.

Full immobilization of both trisaccharides was achieved after 1 hr of incubation and no desorbing effect was seen even at high flow rates, indicative of incorporation into microporous structure of both adsorbents. The results suggest the adsorbing potency of synthetic carbon and hydroxyapatite was behind stable immobilization of A- and B-trisaccharides ligands.

Example 2

Removal and Anti-A and Anti-B Antibodies by Microporous/Mesoporous Synthetic Carbon Beads and Microporous/Mesoporous/Macroporous Hydroxyapatite with Immobilized A- and B-Trisaccharides Ligands.

Synthetic carbon beads or hydroxyapatite with immobilized A- and B-trisaccharides ligands were incubated with donor plasma from blood Type O containing anti-A and anti-B antibodies. Materials were incubated at 37° C. while mixing (45° C., 60 cycles/min, Aliquot Mixer, Model 4561, Ames Company, Ames, Iowa). Samples were collected at 0, 1, and 4 hr intervals. Supernates containing anti-A and anti-B antibodies were screened with gel column agglutination technique determining isoagglutinin IgG and IgM titer (Quest Diagnostics, Madison, N.J.).

While synthetic carbon beads with immobilized A- and B-trisaccharides ligands effectively removed IgG, immobilized hydroxyapatite cleared IgM, reducing initial anti-A and anti B titer levels of 32 by 95% and 99%, respectively. No desorbing effect was observed under high flow rate. The results demonstrate the microporous/mesoporous carbon structure permitted adsorption of 160 kDa IgG, and macroporous structure of hydroxyapatite removed 950 kDa IgM.

Example 3

Periodate-Oxidation of A- and B-Trisaccharides Ligands.

A- or B-trisaccharides were dissolved in 150 mM $NaIO_4$ in sterile water, for 30 minutes, at room temperature, under Laminar Flow Hood Class 100 in clean room. The solution was passed through a 300-mL column of anion exchange resin AG 1-X-8, 100-200 mesh acetate form (Bio-Rad Laboratories, Hercules, Calif.) at 4° C., previously equilibrated with 20 mM acetic acid (Sigma Chemical CO., St. Louis, Mo.), (Eluate A). The column was eluted with Eluate A at temperature 4° C., obtaining fractions collected into sterile, pyrogen free containers (Abbott Laboratories, North Chicago, Ill.). Periodate-oxidized A- or B-trisaccharide fractions were assayed spectrophotometrically at 258 nm. Collected fractions were subjected for sterilization using 0.22 μm vacuum-operated filtration units (NALGENE CO., Rochester, N.Y.; Millipore Co., Bedford, Mass.) and for endotoxin removal by Detoxi-Gel columns (Pierce, Rockford, Ill.) in coldroom (4° C.) under Laminar Flow Hood Class 100. Sterile and pyrogen-free periodate-oxidized A- and B-trisaccharides fractions were freeze-dried by LAB-CONCO Stoppering Tray Dryer in −15° C., with vacuum <10 μ Hg at −40° C. After lyophilization the powder was stored in sterile and sealed containers at −9° C. until use. The results demonstrate the periodate-oxidized A- or B-trisaccharides have a high reactivity with anti-A or anti-B antibodies, respectively.

Example 4

Periodate-Oxidation of PVA.

PVA in the form of beads or as a part of a hollow fiber polymer blend are reacted with 150 mM $NaIO_4$ in sterile water, for 90 minutes, at room temperature, under Laminar Flow Hood Class 100 in clean room, then washed with sterile water for injection. The resulting aldehyde groups are highly reactive with amine groups via Schiff reaction.

Example 5

Immobilization of Periodate-Oxidized A- and B-Trisaccharides Ligands onto Periodate-Oxidized PVA or Polymeric Blends Containing PVA (ie, Polysulfone/PVA Blend).

REACTION No. 1. Schematic representation of covalent immobilization of periodate-oxidized A-trisaccharide to polyvinyl alcohol beads (PVA) treated with sodium periodate (NaIO₄). L-Lysine is covalently attached to periodate-oxidized A-trisaccharide forming Lysine - A-trisaccharide complex with free amine (NH₂) groups reactive with aldehyde group on periodate-oxidized PVA, forming A-trisaccharide-PVA complex via carbonyl bond, which is further reduced to covalent bond by reaction with sodium borohydride (NaBH₄)

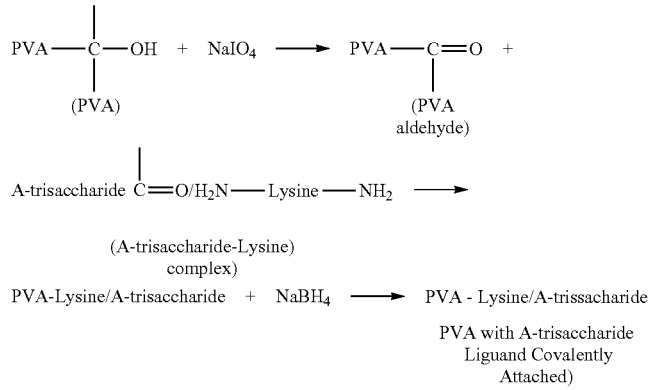

REACTION No. 2. Schematic representation of covalent immobilization of periodate-oxidized B-trisaccharide to polyvinyl alcohol beads (PVA) treated with sodium periodate (NaIO₄). L-Lysine is covalently attached to periodate-oxidized B-trisaccharide forming Lysine - B-trisaccharide complex with free amine (NH₂) groups reactive with aldehyde group on periodate-oxidized PVA, forming B-trisaccharide-PVA complex via carbonyl bond, which is further reduced to covalent bond by reaction with sodium borohydride (NaBH₄).

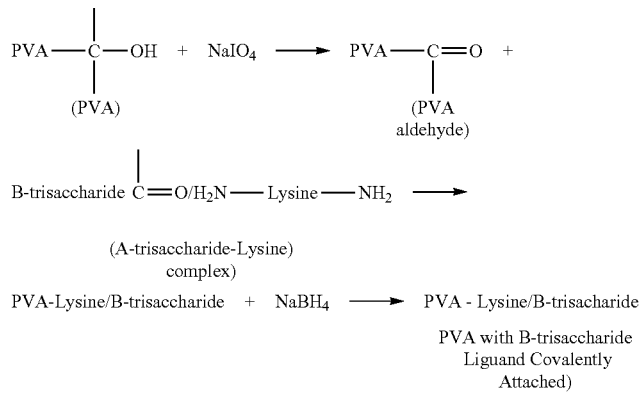

Example 6

Removal of Molecules Contrary to Health by Microporous/Mesoporous Synthetic Carbon Beads from Human Fresh Frozen Plasma.

Two different synthetic carbon bead materials were used to prepare a carbonaceous material of the type disclosed herein and were equilibrated prior to testing, and evaluated for the removal of a range of target molecules from certified human fresh frozen plasma (FFP). Prior to treatment, FFP (Lot No. 9247350, Sera Care Life Sciences, Millford, Mass.) was spiked with human cytokines (QIAGEN, Inc., Valencia, Calif.) at the following concentrations (pg/mL): TNF-α (100-225); IL-1 β (70-110); IL-6 (80-115); IL-8 (225-475); IL-10 (85-125); TGF-β1 (450-1,450); IFN-γ (130-520); MCP-1 (120-160); and CRP (10-15 mg/L). The FFP-adsorbent ratio was similar to that described by Howell et al. (Biomaterials 2006; 27:5286-91). Materials were incubated at 37° C. while mixing. At 0, 1, 2 and 4 hours intervals, samples were collected and analyzed. For endotoxin, nitric oxide (NO=$NO_{2-}$ plus $NO_{3-}$), and hydrogen peroxide ($H_2O_2$), an additional series of experiments were carried out.

Endotoxin, $NO_2$ and $NO_3$, and $H_2O_2$ were applied in concentrations of 0.777±0.082 EU/ml, 30.18±2.96 μM, 238.74±34.86 μM, 30.16±2.96 μM, 238.7±34.9 μM, and 7.76±0.9 nM, respectively. Controls consisted of spiked FFP only, with no adsorbent present.

Materials were incubated at 37° C. while mixing (45 deg., 60 cycles/min, Aliquot Mixer, Model 4561, Ames Company, Ames, Iowa). Samples were collected at 0, 1, and 4 hr intervals.

Figure 4:
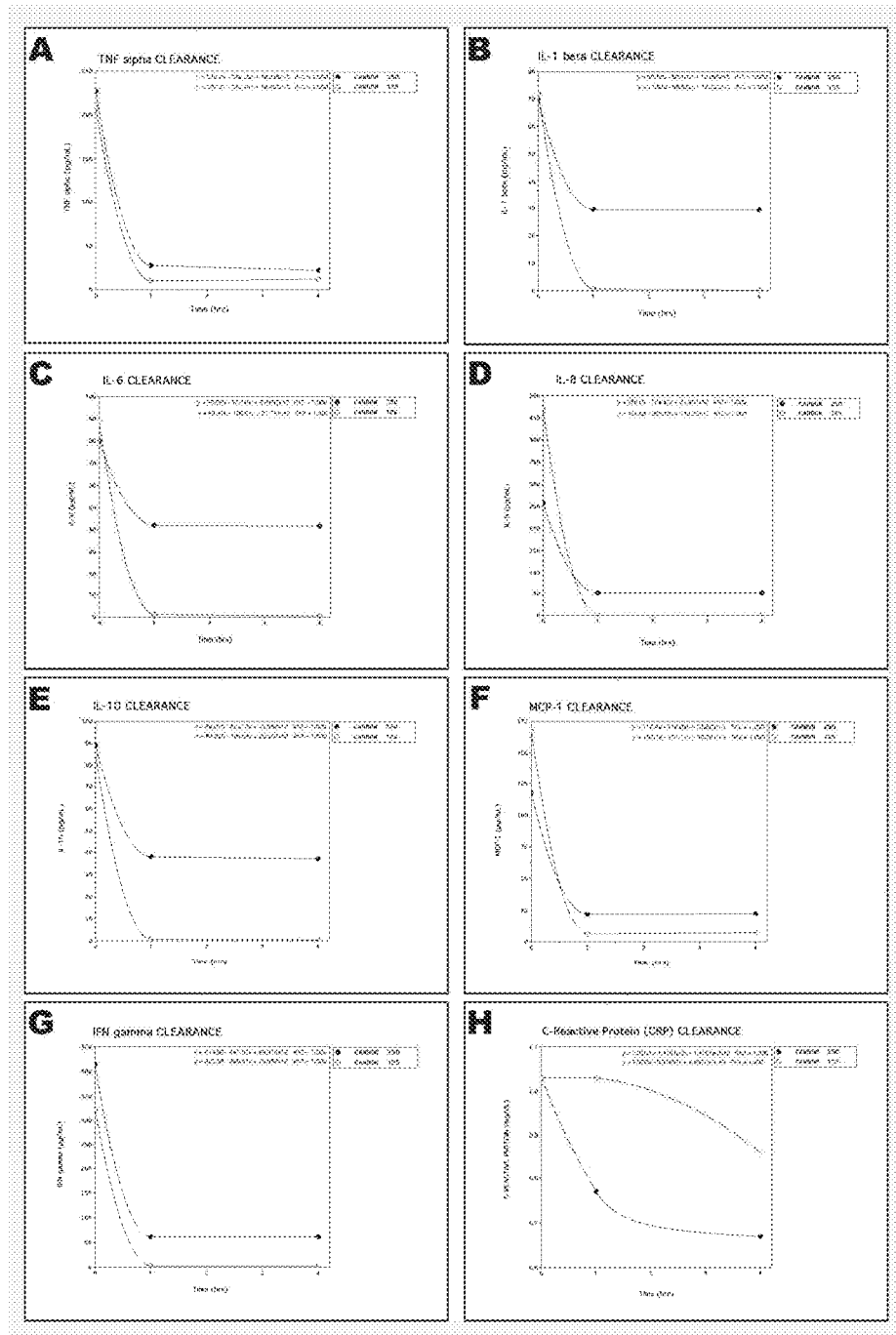
FIG. 4 is a plot of the indicated amount of molecule in a sample of fresh frozen plasma as a function of time following contact with the indicated cleansing formulation.

Cytokines/chemokines (TNF-α, IL-1 β, IL-6, IL-8, IL-10, IFN-γ, MCP-1) were evaluated by the Multi-Analyte Custom ELISArray Kit (CELISA-CMEH0400A, QIAGEN Inc., Valencia, Calif.). This ELISArray Kits was designed to survey a specific panel of cytokines or chemokines involved in autoimmunity, inflammation, or T-cell biology in cell culture supernatant, serum or plasma. The ELISA was conducted in accordance with the protocol specified by the manufacturer. The ELISA was read using Bio-Rad Microplate ELISA reader (Model 3550-UV, Bio-Rad Laboratories, Hercules, Calif.) and calculated using Microplate Manager Software Version 2.2 (Bio-Rad Laboratories). $NO_2/NO_3$=NO concentrations after ethyl were established with the Cayman Chemical Nitrate/Nitrite Assay Kit (Cat. No. 780001, Ann Arbor, Mich.). Endotoxins (LPS) were evaluated with QCL-1000 Limulus Amebocyte Lysate Assay Kit (Product No. 50-647U, BioWhittaker, Walkersville, Md.). CRP was estimated using the commercial diagnostic kit from SIGMA Diagnostics (Procedure No. 371-A, St. Louis, Mo.). $H_2O_2$ was detected by spectrophotometry. The obtained results were tabulated, graphically expressed and analyzed. The results of target molecules clearances are presented in FIG. 4 A-H. FIG. 4 A-H represents effects of microporous/mesoporous synthetic carbon 250 or 125 on plasma clearances of: A: TNF-α; B: IL-β; C: IL-6; D: IL-8; E: IL-10; F: MCP-1; G: IFN-γ; and H: CRP.

ADDITIONAL DISCLOSURE

Disclosed herein is a method of preparing a universal blood product comprising obtaining a blood product wherein the blood product comprises whole blood or plasma; contacting the blood product with (i) hydroxyapatite; (ii) a carbonaceous material comprising at least a mixture of a first carbon particle having macroporous size α and a second carbon particle having macroporous size β; and (iii) at least one support matrix chemically associated with an antigenic determinant. to form a cleansed product; and recovering the cleansed product.

Also disclosed herein is an aspect of any aforementioned subject matter wherein the hydroxyapatite is naturally-occurring, synthetic, or combinations thereof.

Also disclosed herein is an aspect of any aforementioned subject matter wherein the hydroxyapatite has a Brunauer Emmett Teller surface area of from about 200 $m^2/g$ to about 3000 $m^2/g$.

Also disclosed herein is an aspect of any aforementioned subject matter wherein the hydroxyapatite is in the form of beads having a particle size of from about 300 μm to about 1000 μm.

Also disclosed herein is an aspect of any aforementioned subject matter wherein the hydroxyapatite has a unimodal pore size distribution with a pore size ranging from about 2 nm to greater than about 1000 nm.

Also disclosed herein is an aspect of any aforementioned subject matter wherein macroporous size α ranges from about 125 μm to about 250 μm.

Also disclosed herein is an aspect of any aforementioned subject matter wherein macroporous size β ranges from about 250 μm to about 500 μm.

Also disclosed herein is an aspect of any aforementioned subject matter wherein the carbonaceous material further comprises micropores having a pore size range of from about 2 nm to about 50 nm.

Also disclosed herein is an aspect of any aforementioned subject matter wherein the immobilized antigenic determinant comprises a Blood Group A determinant, a Blood Group B determinant, or combinations thereof.

Also disclosed herein is an aspect of any aforementioned subject matter wherein the Blood Group A determinant comprises A-trisaccharides [GalNAcalpha1-3(Fucalpha1-2) Gal.

Also disclosed herein is an aspect of any aforementioned subject matter wherein the Blood Group B determinant comprises B-trisaccharides [Galalpha1-3(Fucalpha1-2) Gal.

Also disclosed herein is an aspect of any aforementioned subject matter wherein the support matrix with chemically associated antigenic determinant is immobilized on a support matrix selected from the group consisting of polyethylene (PE), sepharose; silica; polyoxymethylene (POM), polypropylene (PP), polyvinylchloride (PVC), polyvinyl acetate (PVA), polyvinylidene chloride (PVDC), polystyrene (PS), polytetrafluoroethylene (PTFE), polyacrylate, poly(methyl methacrylate) (PMMA), polyacrylamide, polyglycidyl methacrylate (PGMA), acrylonitrile butadiene styrene (ABS), polyacrylonitrile (PAN), polyester, polycarbonate, polyethylene terephthalate (PET), polyamide, polyaramide, polyethylene glycol (PEG), polyvinylpyrrolidone (PVP), polysulfone (PS), polyethersulfone (PES), polyarylethersulfone (PEAS), ethylene vinyl acetate (EVA), ethylene vinyl alcohol (EVOH), polyamide-imide, polyaryletherketone (PAEK), polybutadiene (PBD), polybutylene (PB), polybutylene terephthalate (PBT), polycaprolactone (PCL), polyhydroxyalkanoate, polyether ether ketone (PEEK), polyether ketone ketone (PEKK), polyether imide (PEI), polyimide, polylactic acid (PLA), polymethyl pentene (PMP), poly(p-phenylene ether) (PPE), polyurethane (PU), styrene acrylonitrile (SAN), polybutenoic acid, poly(4-allylbenzoic acid), poly(glycidyl acrylate), polyglycidyl methacrylate (PGMA), poly(allyl glycidyl ether), poly(vinyl glycidyl ether), poly(vinyl glycidyl urethane), polyallylamine, polyvinylamine, copolymers of said polymers; derivatives of said polymers and combinations thereof.

Also disclosed herein is an aspect of any aforementioned subject matter wherein the support matrix comprise a polysaccharide selected from the group consisting of cellulose, nitrocellulose, chitosan, collagen, starch, cross-linked polysaccharide gels or combinations thereof.

Also disclosed herein is an aspect of any aforementioned subject matter wherein the support matrix is in the form of a bead, a sheet, or a hollow fiber membrane.

Also disclosed herein is an aspect of any aforementioned subject matter further comprising a linker group coupled with both the support matrix and the support matrix with chemically associated antigenic determinant.

Also disclosed herein is an aspect of any aforementioned subject matter wherein the linker group comprises an amino acid.

Also disclosed herein is an aspect of any aforementioned subject matter wherein the cleansed product has an amount of at least one molecule selected from the group consisting of TNF-α, IL-1 β, IL-4. IL-6, IL-8, IL-10, IFN-γ, and TGF-β that is reduced by from about 10% to about 50% when compared to the amount present in the blood plasma product.

Also disclosed herein is an aspect of any aforementioned subject matter wherein the blood plasma product is obtained from a single subject.

Also disclosed herein is an aspect of any aforementioned subject matter wherein the blood plasma product is obtained from at least two subjects.

Also disclosed herein is a hand held device comprising (i) hydroxyapatite; (ii) a carbonaceous material and (iii) a hollow fiber membrane containing at least one support matrix with chemically associated antigenic determinant.

Also disclosed herein is a method of preparing a universal blood product comprising obtaining a blood product wherein the blood product comprises whole blood or plasma; contacting the blood product with (i) hydroxyapatite; (ii) a carbonaceous material comprising at least a mixture of a first carbon particle having macroporous size α and a second carbon particle having macroporous size β; and (iii) at least one support matrix chemically associated with an antigenic determinant. to form a cleansed product; wherein at least one of the hydroxyapatite, carbonaceous material and support matrix is functionalized.

Also disclosed herein is an aspect of any aforementioned subject matter wherein the functionalization comprises the incorporation of polysaccharide.

Also disclosed herein is an aspect of any aforementioned subject matter wherein the polysaccharides are oxidized.

Also disclosed herein is an aspect of any aforementioned subject matter wherein the support matrix comprises periodate oxidized polyvinyl alcohol.

Also disclosed herein is an aspect of any aforementioned subject matter wherein the support matrix further comprises polysaccharides chemically associated with the polyvinyl alcohol via amino acids or peptides.

Also disclosed herein is an aspect of any aforementioned subject matter wherein the amino acids or peptides comprise at least two amine groups.

Also disclosed herein is a device comprising (i) hydroxyapatite; (ii) a carbonaceous material; and (iii) a hollow fiber membrane containing at least one support matrix with chemically associated antigenic determinant.

What is claimed is:

1. A method of preparing a universal blood product comprising:
    obtaining a blood product wherein the blood product comprises whole blood or plasma;
    contacting the blood product with (i) hydroxyapatite, (ii) a carbonaceous material comprising at least a mixture of a first carbon particle comprising pores having a macroporous size α of about 70 nm to about 200 nm and a second carbon particle comprising pores having a macroporous size β of about 70 nm to about 200 nm, wherein macroporous size β is at least twice macroporous size α, (iii) at least one support matrix, and (iv) trisaccharide antigenic determinants to form a cleansed product, wherein the hydroxyapatite, carbonaceous material and support matrix are functionalized with one or more amino acids or peptides; and
    recovering the cleansed product.

2. The method of claim 1 wherein the hydroxyapatite is naturally-occurring, synthetic, or combinations thereof.

3. The method of claim 1 wherein the hydroxyapatite has a Brunauer Emmett Teller surface area of from about 200 $m^2/g$ to about 3000 $m^2/g$.

4. The method of claim 1 wherein the hydroxyapatite is in the form of beads having a particle size of from about 300 μm to about 1000 μm.

5. The method of claim 1 wherein the hydroxyapatite has a unimodal pore size distribution with a pore size ranging from about 2 nm to greater than about 1000 nm.

6. The method of claim 1 wherein the carbonaceous material further comprises mesopores having a pore size range of from about 2 nm to about 50 nm.

7. The method of claim 1 wherein the trisaccharide antigenic determinant comprises a Blood Group A determinant, a Blood Group B determinant, or combinations thereof, and wherein the trisaccharide antigenic determinant is covalently immobilized on a substrate.

8. The method of claim 7 wherein the Blood Group A determinant comprises A-trisaccharides [GalNAcalpha1-3(Fucalpha1-2)Gal].

9. The method of claim 7 wherein the Blood Group B determinant comprises B-trisaccharides [Galalpha1-3(Fucalpha1-2)Gal].

10. The method of claim 1 wherein the at least one support matrix and the trisaccharide antigenic determinant is covalently immobilized on a substrate selected from the group consisting of polyethylene (PE), sepharose; silica; polyoxymethylene (POM), polypropylene (PP), polyvinylchloride (PVC), polyvinyl acetate (PVA), polyvinylidene chloride (PVDC), polystyrene (PS), polytetrafluoroethylene (PTFE), polyacrylate, poly(methyl methacrylate) (PMMA), polyacrylamide, polyglycidyl methacrylate (PGMA), acrylonitrile butadiene styrene (ABS), polyacrylonitrile (PAN), polyester, polycarbonate, polyethylene terephthalate (PET), polyamide, polyaramide, polyethylene glycol (PEG), polyvinylpyrrolidone (PVP), polysulfone (PS), polyethersulfone (PES), polyarylethersulfone (PEAS), ethylene vinyl acetate (EVA), ethylene vinyl alcohol (EVOH), polyamide-imide, polyaryletherketone (PAEK), polybutadiene (PBD), polybutylene (PB), polybutylene terephthalate (PBT), polycaprolactone (PCL), polyhydroxyalkanoate, polyether ether ketone (PEEK), polyether ketone ketone (PEKK), polyether imide (PEI), polyimide, polylactic acid (PLA), polymethyl pentene (PMP), poly(p-phenylene ether) (PPE), polyurethane (PU), styrene acrylonitrile (SAN), polybutenoic acid, poly(4-allyl-benzoic acid), poly(glycidyl acrylate), polyglycidyl methacrylate (PGMA), poly(allyl glycidyl ether), poly (vinyl glycidyl ether), poly(vinyl glycidyl urethane), polyallylamine, polyvinylamine, copolymers of said polymers; derivatives of said polymers and combinations thereof.

11. The method of claim 10 wherein the at least one support matrix comprises a polysaccharide selected from the group consisting of cellulose, nitrocellulose, chitosan, collagen, starch, cross-linked polysaccharide gels or combinations thereof.

12. The method of claim 10 wherein the at least one support matrix is in the form of a bead, a sheet, or a hollow fiber membrane.

13. The method of claim 1 further comprising a linker group coupled with the at least one support matrix.

14. The method of claim 1 wherein the cleansed product has an amount of at least one molecule selected from the group consisting of TNF-α, IL-1 β, IL-4, IL-6, IL-8, IL-10, IFN-γ, and TGF-β that is reduced by from about 10% to about 50% when compared to the amount present in the blood product.

15. The method of claim 1 wherein the blood product is obtained from a single subject.

16. The method of claim 1 wherein the blood product is obtained from at least two subjects.

17. A method of preparing a universal blood product comprising:
    obtaining a blood product wherein the blood product comprises whole blood or plasma;
    contacting the blood product with (i) hydroxyapatite, (ii) a carbonaceous material comprising at least a mixture of a first carbon particle comprising pores having a macroporous size a of about 70 nm to about 200 nm and a second carbon particle comprising pores having a macroporous size β of about 70 nm to about 200 nm, wherein macroporous size β is at least twice macroporous size α; (iii) at least one support matrix, and (iv) trisaccharide antigenic determinants to form a cleansed product; wherein the hydroxyapatite, carbonaceous material and support matrix are functionalized with one or more amino acids or peptides.

18. The method of claim 17 wherein the functionalization further comprises an incorporation of polysaccharide.

19. The method of claim 18 wherein the polysaccharides are oxidized.

20. The method of claim 17 wherein the support matrix comprises periodate oxidized polyvinyl alcohol.

21. The method of claim 20 wherein the support matrix further comprises polysaccharides chemically associated with the polyvinyl alcohol via amino acids or peptides.

22. The method of claim 21 wherein the amino acids or peptides comprise at least two amine groups.

* * * * *